(12) United States Patent
Chang et al.

(10) Patent No.: US 6,368,575 B2
(45) Date of Patent: *Apr. 9, 2002

(54) METHOD FOR INHIBITING CORROSION IN AN AQUEOUS AEROSOL OR FOAM HAIR STYLING COMPOSITION

(75) Inventors: Ching-Jen Chang, Ambler; Andrea Claudette Keenan, Plymouth Meeting; Curtis Schwartz, Ambler, all of PA (US)

(73) Assignee: Rohm and Haas Company, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/391,560

(22) Filed: Sep. 8, 1999

Related U.S. Application Data

(60) Provisional application No. 60/099,898, filed on Sep. 11, 1998.

(51) Int. Cl.$^7$ ................................................. A61K 7/11
(52) U.S. Cl. ..................... 424/47; 424/70.1; 424/70.16; 424/70.23; 514/945; 514/938
(58) Field of Search ............................. 424/40, 43, 45, 424/70.1, 70.23, 47, 70.16; 514/945, 938

(56) References Cited

U.S. PATENT DOCUMENTS

| | | |
|---|---|---|
| 4,196,190 A | 4/1980 | Gehman et al. |
| 5,374,420 A | 12/1994 | Gerstein |
| 5,658,558 A | 8/1997 | Schwartz |
| 5,985,294 A | 11/1999 | Peffly |

FOREIGN PATENT DOCUMENTS

| | | |
|---|---|---|
| EP | 761199 | 3/1997 |
| GB | 1595649 | 8/1981 |
| GB | 2203156 | 10/1988 |
| JP | 54-26250 | 2/1979 |
| JP | 4-59719 | 2/1992 |

OTHER PUBLICATIONS

C.M. Rocafort, (1995) *Spray Technology & Marketing*, Dec. Issue.

N. Shachat and Y.Z. Li, "Phosphate Esters as Primary Anionic Emulsifiers for Acrylic Latex Synthesis" at *Water–Borne & Higher Solids and Powder Coatings Symposium*, New Orleans, LA (USA), Feb. 24–26, 1993.

Johnsen, M.A. (1992). *Spray Technology & Marketing*, Jun. Issue, pp. 32–39.*

* cited by examiner

*Primary Examiner*—Raj Bawa
(74) *Attorney, Agent, or Firm*—Thomas J. Howell

(57) ABSTRACT

A method for improving the corrosion resistance of aerosol or foam hair spray formulations in metal containers is disclosed. In particular, the present invention involves the use of phosphate ester emulsifiers in the preparation of the emulsion polymer hair fixative resins to provide corrosion resistance of the hair styling composition in metal containers without negatively affecting the performance of the hair styling product itself. Use of the selected emulsifiers is particularly useful in non-corrosive aqueous hair styling compositions containing low (80% or less) volatile organic compound (VOC) concentrations.

14 Claims, No Drawings

METHOD FOR INHIBITING CORROSION IN AN AQUEOUS AEROSOL OR FOAM HAIR STYLING COMPOSITION

This is a nonprovisional application of prior pending provisional application Ser. No. 60/099,898 filed Sep. 11, 1998.

BACKGROUND

The present invention relates to aerosol or foam hair styling compositions delivered from metal containers and a method of inhibiting corrosion of the metal container holding the hair styling composition. More particularly, the present invention relates to a method of inhibiting corrosion to tin plate or aluminum aerosol cans caused by the hair spray composition without compromising performance of the hair spray product or without the expense of special can liners. In a preferred embodiment, the present invention also relates to non-corrosive aqueous hair styling compositions containing low (80 weight percent or less) volatile organic compound (VOC) concentrations.

Hair styling products, such as hair sprays, styling gels, spray gels and mousses are used on hair to hold the hair in place. The hair styling products, when applied, form a thin film or weld of resin on the hair, most efficiently in the seam between adjacent hair fibers or at a point where the fibers cross one another, and, as a result, hold the hair in a particular shape or configuration.

Hair styling products can be applied to the hair in several ways. One of the most desirable ways is to formulate the hair fixative resin under pressure in a system containing solvent and propellant. The resin is delivered to hair as a fine mist where the propellant is used to drive the product out of its container onto the hair. Typically, the container is a tin plated metal or aluminum can. Preventing the hair spray formulation from corroding the metal container during storage is a key parameter in formulating an aerosol hair spray suitable for the trade.

Legislation in New York, California and other states mandates that the amount of VOC formulated into hair styling products that are sprayed, such as aerosol and pump hair sprays, must not exceed 80 weight percent (%) in the product. By June 1999, the amount of VOC in hair styling products that are sprayed must be reduced to 55% in California. Other states have enacted similar legislation mandating the reduction of VOC in hair styling products that are sprayed. Present hair styling products in the United States that are sprayed typically have VOC levels of 80% or less. Such VOC include, for example, ethanol, dimethyl ether and hydrocarbons; the most likely replacement for VOC is water.

The introduction of water into the hair styling product accelerates corrosion kinetics (rate of corrosion). Corrosion is also accelerated by presence of certain additives, and reduced in the presence of other additives, called corrosion inhibitors (*Spray Technology & Marketing*, C. M. Rocafort, December, 1995). The presence of certain additives, such as those required to prepare a hair fixative resin (for example, emulsifiers, surfactants, chain transfer agents, initiators and redox agents) may accelerate corrosion to an extent that it cannot be inhibited even with a high concentration of corrosion inhibitors in the formulation or by increasing the pH. These additives, being part of the polymer processing package, cannot be removed or replaced without negatively affecting the ability to prepare the polymer.

The problem addressed by the present invention is to reduce the tendency of hair fixative resin formulations to corrode metal containers in aerosol formulations, particularly low-VOC formulations, without negatively affecting the performance of the hair styling product or its cost effectiveness, and without affecting the ability to prepare the hair fixative resin polymer in high yield with low residual monomer and in a form easily used by the hair styling composition formulator.

U.S. Pat. No. 4,196,190 discloses acrylic hair fixative resins containing 10–30% of an alkyl acrylate, 41–60% of methyl methacrylate, 5–20% of hydroxyethyl methacrylate and 10–30% of methacrylic acid. Although disclosing that water can be used in a hair styling composition containing the acrylic hair fixative resins, this reference does not disclose or suggest methods for overcoming the problems associated with hair styling compositions regarding corrosion. U.S. Pat. No. 5,658,558, although disclosing how to improve the performance of acrylic resins in low-VOC systems, also does not disclose how to overcome corrosion problems.

The use of phosphate esters as emulsifiers to prepare acrylic emulsion polymers is disclosed in "Phosphate Esters as Primary Anionic Emulsifiers for Acrylic Latex Synthesis" by N. Shachat and Y. Z. Li, at *Water-Borne & Higher Solids and Powder Coatings Symposium*, New Orleans, La. (USA), Feb. 24–26, 1993. GB Patent No. 2,203,156 discloses corrosion resistant compositions for metal surfaces coated with acrylic resin and organic phosphate/phosphite mixtures. Neither of these references discloses how to overcome the problems associated with aerosol hair styling compositions regarding corrosion.

The present invention seeks to overcome deficiencies of the prior art hair fixative resin technology by using hair fixative resins prepared by emulsion polymerization using selected emulsifiers as processing aids to minimize corrosion in the hair styling formulation while retaining other beneficial hair fixative properties.

STATEMENT OF INVENTION

One embodiment of the present invention provides an aqueous aerosol or foam hair styling composition comprising (a) from 1 to 15 weight percent of at least one acrylic hair fixative resin, based on total weight of the aqueous aerosol or foam hair styling composition, wherein the acrylic hair fixative resin is a polymer comprising as polymerized units from 2 to 100 weight percent of at least one $(C_1–C_{12})$alkyl (meth)acrylate, based on total weight of the acrylic hair fixative resin; and (b) from 10 to 70 weight percent of at least one propellant, based on total weight of the aqueous hair styling composition; wherein the hair fixative resin is an emulsion polymer prepared in the presence of a phosphate ester emulsifier.

In another embodiment, the present invention provides the aforementioned aqueous aerosol or foam hair styling composition further comprising volatile organic compounds in a concentration up to 98 weight percent, based on total weight of the aqueous hair styling composition.

In a further embodiment, the present invention provides an improved method for inhibiting corrosion in an aqueous aerosol or foam hair styling composition as described as above, wherein the improvement comprises preparing the acrylic hair fixative resin by emulsion polymerization in the presence of a phosphate ester emulsifier.

DETAILED DESCRIPTION

The method of the present invention is useful for improving the corrosion resistance of aerosol or foam hair styling formulations when the hair styling formulation is provided in metal containers, such as aerosol cans. We have found that the use of certain selected emulsifiers, that is, phosphate esters, in the preparation of the emulsion polymer hair fixative resins surprisingly improves the corrosion resistance of the hair styling composition in metal containers without negatively affecting the performance of the hair styling product itself.

By an "aqueous hair styling composition" we mean a hair spray or mousse (aerosol or foam) that is used on hair to hold the hair in a particular shape or configuration. Preferably, the hair styling composition in the present invention is a hair spray.

As used herein, all percentages referred to will be expressed in weight percent (%) unless specified otherwise.

The aqueous hair styling compositions typically will contain at least 2% and up to 98% water, more typically, from 25 to 70% water, based on the total weight of the aqueous hair styling composition. By "low-VOC" we mean the hair styling composition contains 80% or less volatile organic compounds, that is, typically 10% or more of water. Preferably, the hair styling composition contains less than 70%, and more preferably 55% or less, VOC. Optionally, the hair styling composition may contain no VOC.

The term "(meth)acrylate" means methacrylate or acrylate. The term "(meth)acrylic acid" means methacrylic acid or acrylic acid. As used herein, the term "unsaturated dicarboxylic acid monomer" refers to monoethylenically unsaturated dicarboxylic acids containing 4 to 8, preferably from 4 to 6, carbon atoms per molecule and anhydrides of the corresponding dicarboxylic acids. Dicarboxylic acid monomers include, for example, maleic acid, maleic anhydride, fumaric acid, α-methylene glutaric acid, itaconic acid, itaconic anhydride, citraconic acid, mesaconic acid, cyclohexenedicarboxylic acid, and water-soluble salts thereof.

When the word "soluble" is used to further describe a compound, such as for example the "soluble hair fixative resins," we mean herein that the compound described is soluble in the hair styling composition. When the word "insoluble" is used to further describe a compound, such as for example the "insoluble hair fixative resins," we mean herein that the compound described is insoluble in the hairstyling composition.

As used herein, VOC are compounds containing at least one carbon atom and are typically used as solvents or propellants in hair styling compositions. VOC include, for example, $C_1-C_{12}$ straight or branched chain alcohols such as methanol, ethanol, propanol, isopropanol and butanol; $C_1-C_{12}$ straight or branched chain hydrocarbons such as methane, ethane, propane, isopropane, isobutane, pentane, isopentane and butane; or ethers such as dimethyl ether and dimethoxymethane. Preferred VOC are selected from one or more of ethanol, isopropanol, n-propanol, dimethoxymethane, dimethylether and $C_1-C_{12}$ straight or branched chain hydrocarbons.

Soluble hair fixative resins that are useful in the present invention are soluble in the hair styling composition "as is" or upon neutralization of some or all of any acid groups contained in the soluble hair fixative resins. The soluble hair fixative resins, when sprayed, preferably have viscosities less than $30 \times 10^{-3}$ pascal·seconds (Pa·sec) (or 30 centipoise), and more preferably less than $25 \times 10^{-3}$ Pa·sec, in an aerosol concentrate.

In general, polymers useful as hair fixative resins in practicing the present invention may be any acrylic emulsion polymer containing as polymerized units from 2 to 100%, preferably from 5 to 95%, more preferably from 45 to 90%, of at least one $(C_1-C_{12})$alkyl (meth)acrylate, based on total weight of the acrylic hair fixative resin. Preferably, the $(C_1-C_{12})$alkyl (meth)acrylate comprises substantially $(C_1-C_{10})$alkyl (meth)acrylates, and more preferably $(C_1-C_8)$alkyl (meth)acrylates.

Optionally, the polymer may contain, as polymerized units, from 2 to 70%, and preferably from 2 to 26%, of at least one hydroxyalkyl (meth)acrylate. The alkyl group of the hydroxyalkyl (meth)acrylate is preferably a $(C_1-C_5)$ alkyl group. For example, the hydroxyalkyl (meth)acrylate is preferably selected from one or more of hydroxyethyl (meth)acrylate, hydroxypropyl (meth)acrylate, hydroxybutyl (meth)acrylate and hydroxypentyl (meth)acrylate. More preferably the hydroxyalkyl (meth)acrylate is selected from one or more of hydroxyethyl methacrylate and hydroxypropyl acrylate.

Optionally, the polymer may contain, as polymerized units, from 2 to 50% of at least one $C_3-C_8$ monoethylenically unsaturated monocarboxylic acid monomer. The $C_3-C_8$ monoethylenically unsaturated monocarboxylic acid monomer is preferably selected from one or more of acrylic acid, methacrylic acid and crotonic acid. More preferably, the $C_3-C_8$ monoethylenically unsaturated monocarboxylic acid is methacrylic acid.

Optionally, the polymer may contain, as polymerized units, from 1 to 25% of at least one $C_4-C_8$ monoethylenically unsaturated dicarboxylic acid monomer. The $C_4-C_8$ monoethylenically unsaturated dicarboxylic acid monomer is preferably selected from one or more of itaconic acid, maleic acid and the corresponding anhydrides. Preferably, the $C_4-C_8$ monoethylenically unsaturated dicarboxylic acid monomer is itaconic acid.

Optionally, the polymer may also contain, as polymerized units, additional vinyl monomers, such as for example, vinyl acetate, vinyl neodecanoate, vinylpyrrolidone, octylacrylamide and t-butylaminoethyl methacrylate.

Preferably, the hair fixative resin comprises as polymerized units (i) from 5 to 95%, and more preferably from 45 to 90%, of at least one $(C_1-C_{12})$alkyl (meth)acrylate, (ii) from 2 to 70%, and more preferably from 2 to 26%, of at least one hydroxyalkyl (meth)acrylate and (iii) from 2 to 50%, more preferably from 2 to 30%, and most preferably from 12 to 26%, of at least one $C_3-C_8$ monoethylenically unsaturated monocarboxylic acid monomer. More preferably the hair fixative resin further comprises as polymerized units from 1 to 25% of at least one $C_4-C_8$ monoethylenically unsaturated dicarboxylic acid monomer. Most preferably the $C_4-C_8$ monoethylenically unsaturated dicarboxylic acid monomer is from 2 to 10% of itaconic acid.

Preferably, the $(C_1-C_{12})$alkyl (meth)acrylate is selected from one or more $(C_1-C_5)$alkyl (meth)acrylates such as, for example, methyl (meth)acrylate, ethyl (meth)acrylate, propyl (meth)acrylate, butyl (meth)acrylate and pentyl (meth) acrylate.

More preferably the $(C_1-C_{12})$alkyl (meth)acrylate component comprises at least one $(C_1-C_3)$alkyl methacrylate and at least one $(C_2-C_5)$alkyl acrylate. Most preferably the $(C_1-C_{12})$alkyl (meth)acrylate component comprises methyl methacrylate and butyl acrylate. The amount of the at least one $(C_1-C_3)$alkyl methacrylate in the hair fixative resin is preferably from 5 to 71%, more preferably from 41 to 60%, based on the total monomers used to form the hair fixative resin. The amount of $(C_2-C_5)$alkyl acrylate is preferably from 2 to 67% and more preferably from 10 to 30%, based on the total monomer used to form the acrylic hair fixative resin. Preferably, the ($C_1$–$C_{12}$)alkyl (meth)acrylate is from 2 to 67 weight percent of at least one ($C_2$–$C_5$)alkyl acrylate and from 5 to 71 weight percent of methyl methacrylate.

The proportions of the monomers comprising the acrylic hair fixative resin are selected to provide for an optimum hydrophilic/hydrophobic balance. This optimum balance provides, especially in a low-VOC hair styling composition, curl retention under humid conditions, moisture resistance, shampoo removability, feel or stiffness, and desirable aesthetics to the hair, such as minimal flaking of the hair fixative resin.

The acrylic hair fixative resins are preferably added to the hair styling composition to provide a total concentration of from 1 to 15%, more preferably from 4 to 7%, of the acrylic hair fixative resins, based on the total weight of the hair styling composition.

The acrylic hair fixative resins may be prepared by conventional emulsion polymerization methods well known to those skilled in the art. Preferably, the acrylic hair fixative resins are made by a continuous in-line emulsification process. U.S. Pat. Nos. 3,245,932, 3,453,245 and 4,196,190 may be consulted for further general and specific details on suitable emulsion polymerization methods. For the purposes of the present invention, emulsifiers used to prepare the hair fixative resins comprise one or more phosphate ester emulsifiers. Preferably, the phosphate ester emulsifier is selected from one or more long-chain alkyloxypoly(alkyleneoxide), long-chain alkylaryloxypoly(alkyleneoxide), long-chain alkyl and long-chain alkylaryl mono- and di-esters of phosphoric acid, such as ($C_8$–$C_{18}$)alkylaryloxypoly(alkyleneoxide), ($C_{10}$–$C_{18}$)alkyloxypoly(alkyleneoxide), ($C_{10}$–$C_{18}$)alkyl, and ($C_8$–$C_{18}$)alkylaryl mono- and di-esters of phosphoric acid. More preferably, the phosphate ester emulsifier is one or more ($C_8$–$C_{18}$)alkylaryloxypoly(alkyleneoxide) and ($C_{10}$–$C_{18}$)alkyloxypoly(alkyleneoxide) mono- and di-esters of phosphoric acid, and corresponding salts (such as, for example, sodium and ammonium salts).

Preferably the poly(alkyleneoxide) moieties of the phosphate ester are based on one or more of ethylene oxide and propylene oxide; the average number of alkylene oxide units per group is typically from 2 to 100, preferably from 3 to 50, more preferably from 4 to 20, and most preferably from 6 to 10. The long-chain alkyl and long-chain alkylaryl groups are typically selected from one or more ($C_8$–$C_{18}$)alkylaryl and ($C_{10}$–$C_{18}$)alkyl groups; preferred long-chain alkyl and long-chain alkylaryl groups include, for example, nonylphenyl, t-octylphenyl, lauryl, tridecyl and stearyl.

Suitable acrylic hair fixative resins for use in the hair styling compositions include, for example, those described in U.S. Pat. No. 4,196,190, that is, polymers containing 10–30% of an alkyl acrylate, 41–60% of methyl methacrylate, 5–20% of hydroxyethyl methacrylate and 10–30% of methacrylic acid. The acrylic hair fixative resin may be soluble or insoluble in the hair styling composition.

When the acrylic hair fixative resins contain acidic groups, such as carboxylic acid groups, these may be neutralized by conventional techniques with at least one base to promote solubility of the resins in the hair styling composition. The acrylic hair fixative resins are preferably neutralized with at least one neutralizer.

Bases that will neutralize the soluble hair fixative resins may be selected from one or more amines, alkali or alkaline earth metal hydroxides, and ammonium hydroxide. Suitable amine neutralizers include, for example, 2-amino-2-methyl-1,3-propanediol, 2-amino-2-methyl-1-propanol, N,N-dimethyl- 2-amino-2-methyl-1-propanol, mono-isopropanolamine, triisopropanolamine, ethanolamine, triethanolamine and morpholine. Suitable alkali or alkaline earth metal hydroxides include, for example, sodium hydroxide and potassium hydroxide. Preferably, the neutralizer is selected from one or more of 2-amino-2-methyl-1,3-propanediol, 2-amino-2-methyl-1-propanol, N,N-dimethyl-2-amino-2-methyl-1-propanol, potassium hydroxide, triethanolamine and triisopropanolamine.

The amount of neutralizer added to the hair styling composition is that amount needed to provide solubility of the soluble hair fixative resins in the hair styling composition. Typically from 5 to 100%, preferably from 10 to 100%, more preferably from 50 to 100%, and most preferably from 75 to 100%, based on molar equivalents, of the acid groups in the hair fixative resins are neutralized.

The aqueous hair resin composition that suspends or dissolves the acrylic hair fixative resin before being added to the hair styling composition is preferably an aqueous emulsion that was obtained from the process that produced the acrylic hair fixative resins. The aqueous emulsion, hereinafter called the "acrylic hair resin emulsion," is typically unneutralized and has a pH from 1.5 to 4.5; optionally the emulsion may be partially neutralized. The acrylic hair resin emulsion preferably contains from 30 to 60% of the acrylic hair fixative resins, greater than 30% water, based on total weight of the emulsion; and 0.05 to 5%, preferably from 0.1 to 2%, and more preferably from 0.3 to 1%, of one or more phosphate ester emulsifiers, based on total weight of the hair fixative polymer. Preferably, the acrylic hair resin emulsion is prepared substantially in the absence of sulfate or sulfonate type emulsifiers (such as sodium lauryl sulfate, sodium tridecylether sulfate, diester sulfosuccinates, and alkyl or aryl polyether sulfonates), that is, less than 0.05%, more preferably less than 0.01%, and most preferably zero %, based on total weight of the hair fixative polymer.

In addition to the soluble hair fixative resins, the insoluble hair fixative resins and water, the hair styling composition may also contain surfactants, solvents, propellants, and other preservatives.

One or more surfactants may be added to the hair styling composition, typically to reduce the surface tension of the composition. When surfactants are present in the hair styling composition, they are preferably present at a concentration of from 0.001 to 1%, based on the total weight of the composition. The surfactants that may be used in the hair styling composition include, for example, anionic, cationic, nonionic and amphoteric surfactants. For example, suitable surfactants include PPG 28 Buteth 35, PEG 75 lanolin, perfluoropolymethyl isopropyl ether, octoxynol-9, PEG-25 hydrogenated castor oil, polyethylene terephthalate, polyethylene glycol 25 glyceryl trioleate, oleth-3 phosphate, PPG-5-ceteth-10 phosphate, PEG-20 methyl glucose ether, glycereth-7-triacetate and n-alkyl substituted lactam (such as n-octyl pyrrolidone).

One or more plasticizers may be added to the hair styling composition of the present invention. When plasticizers are present in the hair styling composition, they are preferably present at a concentration of from 0.001 to 1%, based on the total weight of the composition. The plasticizers that may be used in the hair styling composition include, for example, dimethicone copolyol, dimethicone, phenyltrimethicones, trialkylcitrates, and others that are known and typically used in the art.

One or more solvents may be added to the hair styling composition of the present invention. When solvents are added to the hair styling composition they preferably comprise up to 70%, more preferably up to 55%, of the total hair styling composition, based on the total weight of the hair styling composition. Suitable solvents include, for example, $C_2$–$C_6$ organic alcohols (such as ethanol, isopropanol, n-propanol) and acetone.

In a low-VOC hair styling composition using an aerosol spray, one or more propellants are used. Preferably the propellants are used at a total concentration of from 10 to 70%, more preferably from 30 to 60%, based on the total weight of the hair styling composition. Suitable propellants include, for example, n-butane, isobutane, dimethyl ether, 1,1-difluoroethane, chloro-difluoroethane, chlorodifluoromethane and other chlorofluorocarbons. Preferred propellants are selected from one or more of dimethyl ether, 1,1-difluoroethane, n-butane and isobutane. These propellants are commercially available from a variety of manufacturers.

Preservatives that may be used in the hair styling composition include, for example, one or more of isothiazolones, iodopropynylbutyl carbamate, benzyl alcohol, imidazolidinylurea and alkyl parabens. A preferred antimicrobial agent is iodopropynylbutylcarbamate (commercially available from Lonza Inc., Fairlawn, N.J.) The preservatives preferably comprise from 0.001 to 1% active ingredient in the hair fixative resin emulsion.

Other additives, such as those commonly used by those skilled in the art, may be added to the hair styling composition. The other additives used in the hair styling composition will depend upon the type of hair styling composition desired. Other additives include, for example, one or more of fragrances; moisturizers (such as hydrolyzed silk protein and hydrolyzed wheat protein); detangling aids such as panthenol; conditioning agents (U.S. Pat. No. 5,164,177 may be consulted for further general and specific details on suitable conditioning agents); emulsifiers; antistatic aids; extracts; proteins; vitamins; dyes; tints; colorants; UV protectors; and corrosion inhibitors. The other additives typically comprise from 0.005 to 5%, and more preferably from 0.01 to 1%, of the hair styling composition.

Additional other additives, as well as additional surfactants, solvents, other preservatives, and thickeners, that may be suitable in the hair styling composition may be found in the International Cosmetic Ingredients Dictionary, 5th Edition, 1993, published by the Cosmetics Toiletries Fragrances Association (CFTA), Washington D.C.

Examples 1–4A describe polymer preparations representative of hair fixative resin polymers of the present invention, including comparative compositions. All ratios, parts and percentages are expressed by weight unless otherwise specified, and all reagents used are of good commercial quality unless otherwise specified. Abbreviations for monomers, emulsifiers and other materials described in the Examples are presented in Table 1. Hair fixative resin monomeric unit composition/emulsifier data are summarized in Table 2.

TABLE 1

| | |
|---|---|
| BA | Butyl Acrylate |
| IBOA | Isobornyl Acrylate |
| IBOMA | Isobornyl Methacrylate |
| MMA | Methyl Methacrylate |
| HEMA | Hydroxyethyl Methacrylate |
| MAA | Methacrylic Acid |
| IA | Itaconic Acid |

TABLE 1-continued

| | |
|---|---|
| DDM | Dodecyl Mercaptan |
| SLS | Sodium Lauryl Sulfate |
| PPE-1 | Tridecyloxypoly(ethyleneoxide)$_6$ Phosphate (55/45)Mono/Diester |
| PPE-2 | Tridecyloxypoly(ethyleneoxide)$_{10}$ Phosphate (60/40)Mono/Diester |
| PPE-3 | t-Octylphenoxypoly(ethyleneoxide)$_{7.5}$ Phosphate Monoester |

TABLE 2

| Polymer ID# | Hair Fixative Resin Composition |
|---|---|
| 1 | 25 BA/47 MMA/10 HEMA/13 MAA/5 IA with PPE-1 |
| 1A-comp | 25 BA/47 MMA/10 HEMA/13 MAA/5 IA with SLS |
| 1B | 25 BA/47 MMA/10 HEMA/13 MAA/5 IA with PPE-2 |
| 1C | 25 BA/47 MMA/10 HEMA/13 MAA/5 IA with PPE-3 |
| 2-comp | 25 BA/47 MMA/10 HEMA/18 MAA with SLS* |
| 2A | 25 BA/47 MMA/10 HEMA/18 MAA with PPE-1* |
| 3-comp | 18 BA/7 IBOA/47 MMA/10 HEMA/18 MAA with SLS |
| 3A | 18 BA/7 IBOA/47 MMA/10 HEMA/18 MAA with PPE-1 |
| 4-comp | 21 BA/4 IBOMA/47 MMA/10 HEMA/13 MAA/5 IA with SLS |
| 4A | 21 BA/4 IBOMA/47 MMA/10 HEMA/13 MAA/5 IA with PPE-1 |

*0.3% (based on total monomer) additional PPE-1 added before corrosion testing

The corrosion performance data reported in Table 3 are based on visual ratings for 3 different "cans" (for the same polymer composition) by 3 different observers; this corresponds to 9 observations for each corrosion rating of a particular polymer/emulsifier composition; the average corrosion rating value and standard deviations are given. Example 5 describes the corrosion test method used to evaluate the different hair fixative resin compositions. Visual corrosion ratings were based on the following scale:

| | |
|---|---|
| No corrosion | 0 |
| Slight corrosion | 1 |
| Moderate corrosion | 3 |
| Severe corrosion | 5 |

Comparisons of corrosion data for different hair fixative resin formulations are only valid when the pH values of the compositions are similar, that is, within ±0.5 pH units, preferably within ±0.2 pH units or less. As the pH decreases below about 8, the overall degree of corrosion is greater and differences between he polymer/phosphate-ester emulsifier compositions versus the polymer/sulfate-emulsifier compositions are magnified. As the pH approaches 9, the overall degree of corrosion generally decreases; however, there is still a significant observable difference between polymer compositions prepared with phosphate-ester emulsifiers versus those prepared with sulfate emulsifiers. For example, the difference in corrosiveness (ΔC) between SLS and phosphate ester prepared emulsion polymers ranges from +0.4 up to +4 for Polymer Compositions 1, 2 and 3 (Table 3).

Aerosol hair styling compositions may have pH values from 5 to 10, preferably from 6 to 9.5, and more preferably from 7 to 8.5. Although corrosion is generally less of a problem in aerosol containers for compositions having pH values above 8.5 (depending on the hair fixative resin composition), the higher pH values may detract from the overall hair fixative resin properties due to plasticization of the hair fixative resin. This may lead to poorer high humidity curl retention, lower stiffness and increased tackiness of the resin film on the hair. Residues from the hair fixative resin formulation (such as sulfate and sulfonate emulsifiers) may promote corrosion regardless of the pH. It is, therefore, advantageous to be able to formulate aerosol hair styling compositions at a pH that allows solubility or dispersibility in the hair styling formulation and good shampoo removability without overneutralizing (that is, increasing the pH) the hair fixative resin in the hair styling composition. Use of hair fixative resins prepared according to the method required by the present invention allows for improved corrosion resistance over a wide pH range without compromising hair styling performance of the hair fixative resin and also allows the hair styling composition formulator to use lower levels of conventional corrosion inhibitors, further lessening the likelihood of negatively affecting hair fixative resin performance.

Hair styling performance properties (such as curl retention, stiffness, drying time, tackiness and film clarity) of hair fixative resins based on Polymer Compositions 1–4 are unaffected by the emulsifier used to prepare the polymer.

TABLE 3

| Polymer Composition | Corrosion Rating | Standard Deviation | pH | ΔC** |
|---|---|---|---|---|
| 1 | 0.2 | 0.3 | 8.7 | +1.2 |
| 1A-comp | 1.4 | 0.6 | 8.7 | — |
| 1B | 0.2 | 0.1 | 8.8 | +1.2 |
| 1C | 0.4 | 0.25 | 8.9 | +1.0 |
| 2-comp | 4.3 | 0.85 | 7.3 | — |
| 2A | 2.2 | 0.9 | 7.2 | +2.1 |
| 2-comp | 4.0* | 0.0 | 6.4 | — |
| 2A | 0.0* | 0.0 | 6.5 | +4.0 |
| 3-comp | 0.7 | 0.8 | 8.8 | — |
| 3A | 0.3 | 0.2 | 8.4 | +0.4 |
| 4A | 1.2 | 0.3 | 8.8 | — |
| 4-comp | 0.8 | 0.9 | 8.8 | — |

*based on average of 6 observations, others on 9 observations
**difference in corrosion rating between SLS polymer and phosphate ester polymer

EXAMPLE 1

To a three liter, four-neck round bottom flask equipped with overhead stirrer, condenser, nitrogen adapter and a thermocouple was added 43.5 grams (g) itaconic acid (IA) powder, 255.0 g deionized water and 8.5 g of 25% (in water) mixed phosphate ester emulsifier as ammonium salt (55/45 weight ratio mixture of mono-tridecyloxypoly (ethyleneoxide) and di-tridecyloxypoly(ethyleneoxide) esters of phosphoric acid having an average of 6 ethyleneoxide units per group [PPE-1 in Table 1]; available as Rhodafac RS-610A from Rhône-Poulenc; Rhodafac is a trademark of Rhône-Poulenc Inc.). With the nitrogen turned on, the reactor and contents were heated to 83° C. and an initiator solution of 2.2 g ammonium persulfate and 17.5 g deionized water was added with stirring. After the initiator solution was charged, 50 g of monomer emulsion, from a monomer emulsion containing 388 g deionized water, 12.75 g mixed phosphate ester emulsifier, 408.9 g methylmethacrylate (NMA), 217.5 g butylacrylate (BA), 87 g hydroxyethylmethacrylate (HEMA), 113.1 g methacrylic acid (MA) and 11.0 g n-dodecyl mercaptan (DDM), was charged to the reactor. The remaining monomer emulsion feed was then fed over 120 minutes while maintaining a temperature of 83° C. A cofeed initiator solution containing 0.73 g ammonium persulfate and 79.0 g deionized water was gradually added simultaneously with the monomer emulsion feed over 120 minutes.

After the monomer emulsion and initiator feeds were complete, the reaction mixture was "chased" with a ferrous sulfate, t-butyl hydroperoxide, ammonium persulfate and d-isoascorbic acid combination to reduce residual monomer levels. The reaction mixture was then cooled to room temperature and filtered. The composition of the resulting polymer was 47 MMA/25 BA/10 HEMA/13 MAA/5 IA. The amount of PPE-1 emulsifier was 0.6%, based on total monomer weight.

EXAMPLE 1A
(Comparative)

An emulsion polymer composition was again prepared according to the procedure in Example 1 except for the surfactant employed and its total amount based on monomer. Sodium lauryl sulfate (28% aqueous solution) was charged at 8.5 g as part of initial reactor charge and 4.25 g as part of the monomer emulsion.

EXAMPLES 1B–4A

Additional emulsion polymer compositions (1B, 1C, 2-comparative, 2A, 3-comparative, 3A, 4-comparative and 4A) were prepared similarly to Examples 1 or 1A and are summarized in Table 2 for monomeric unit composition and emulsifier used.

EXAMPLE 5
Corrosion Test Method

Screening tests for corrosion of aqueous based aerosol cans were based on the DuPont Closed Cell Galvanic test (described in *Spray Technology & Marketing*, M. E. Boulden, April 1993); this test provides a good prediction of long term corrosion stability. The galvanic corrosion evaluations were conducted for 96 hours at ambient temperature using tin plate cans containing 65 to 70 parts dimethyl ether propellant and 30 to 35 parts concentrate. The concentrate was composed of sufficient hair fixative resin solids to provide 5% total solids in the resulting hair styling composition, based on combined weight of concentrate and propellant. The numerical corrosion rating was an overall visual assessment of the entire interior of the can, for example, joints, base, walls, seams and dome.

We claim:

1. An aqueous aerosol or foam hair styling composition comprising:

(a) from 1 to 15 weight percent of at least one acrylic hair fixative resin, based on total weight of the aqueous aerosol or foam hair styling composition, wherein the acrylic hair fixative resin comprises as polymerized units from 5 to 95 weight percent of at least one ($C_1$–$C_{12}$)alkyl (meth)acrylate, and from 2 to 50 weight percent of at least one $C_3$–$C_8$ monoethylenically unsaturated monocarboxylic acid monomer, based on total weight of the acrylic hair fixative resin;

(b) from 10 to 70 weight percent of at least one propellant, based on total weight of the aqueous hair styling composition; and (c) from 0.1 to 2 weight percent of a phosphate ester emulsifier selected from the group consisting of ($C_8$–$C_{18}$)alkylaryloxypoly(alkyleneoxide) monoesters of phosphoric acid, ($C_8$–$C_{18}$)alkylaryloxypoly (alkyleneoxide)diesters of phosphoric acid, ($C_{10}$–$C_{18}$) alkyloxypoly(alkyleneoxide) monoesters of phosphoric acid, ($C_{10}$–$C_{18}$)alkyloxypoly(alkyleneoxide)diesters of phosphoric acid, salts thereof, and mixtures thereof, based on total weight of hair fixative resin; wherein the hair fixative resin is an emulsion polymer prepared in the absence of sulfate or sulfonate emulsifiers and in the presence of said phosphate ester emulsifier and wherein the composition has a pH from 6 to 9.5.

2. The composition of claim 1 further comprising at least one neutralizer.

3. The composition of claim 2 wherein the neutralizer is selected from the group consisting of 2-amino-2-methyl-1,3-propanediol, 2-amino-2-methyl-1-propanol, N,N-dimethyl-2-amino-2-methyl-1-propanol, potassium hydroxide, triethanolamine, triisopropanolamine and mixtures thereof.

4. The composition of claim 1 further comprising volatile organic compounds in a concentration up to 98 weight percent, based on total weight of the aqueous hair styling composition.

5. The composition of claim 4 wherein the volatile organic compounds are selected from the group consisting of ethanol, isopropanol, n-propanol, dimethoxymethane, dimethylether, $C_1$–$C_{12}$ straight or branched chain hydrocarbons, and mixtures thereof.

6. The composition of claim 4 wherein the volatile organic compounds concentration is 80 weight percent or less.

7. The composition of claim 1 wherein the hair fixative resin further comprises as polymerized units from 1 to 25 weight percent of at least one $C_4$–$C_8$ monoethylenically unsaturated dicarboxylic acid monomer.

8. The composition of claim 1 wherein the hair fixative resin further comprises as polymerized units from 2 to 70 weight percent of at least one hydroxyalkyl (meth)acrylate.

9. The composition of claim 8 wherein:
(a) the ($C_1$–$C_{12}$)alkyl (meth)acrylate is from 2 to 67 weight percent of at least one ($C_2$–$C_5$)alkyl acrylate and from 5 to 71 weight percent of methyl methacrylate;
(b) the hydroxyalkyl (meth)acrylate is from 2 to 26 weight percent of hydroxyethyl methacrylate; and
(c) the $C_3$–$C_8$ monoethylenically unsaturated monocarboxylic acid monomer is from 2 to 30 weight percent of methacrylic acid.

10. The composition of claim 9 wherein the hair fixative resin further comprises as polymerized units from 1 to 25 weight percent of at least one $C_4$–$C_8$ monoethylenically unsaturated dicarboxylic acid monomer.

11. The composition of claim 1 wherein the propellant is selected from the group consisting of dimethyl ether, 1,1-difluoroethane, n-butane, isobutane, and mixtures thereof.

12. The composition of claim 1 wherein the hair fixative resin is prepared in the presence of less than 0.05 percent of sulfate or sulfonate emulsifiers, based on total weight of the hair fixative resin.

13. An improved method for Inhibiting corrosion in a metal container comprising use of the hair styling composition of claim 1 in aerosol cans.

14. The method of claim 13 wherein the hair fixative resin of the hair styling composition further comprises as polymerized units from 2 to 70 weight percent of at least one hydroxyalkyl (meth)acrylate.

* * * * *

UNITED STATES PATENT AND TRADEMARK OFFICE
CERTIFICATE OF CORRECTION

PATENT NO. : 6,368,575 B2
DATED : April 9, 2002
INVENTOR(S) : Ching-Jen Chang

It is certified that error appears in the above-identified patent and that said Letters Patent is hereby corrected as shown below:

Column 9,
Line 57, "(NMA)" should be -- (MMA) --
Line 59, "(MA)" should be -- (MAA) --

Signed and Sealed this

Eighth Day of October, 2002

Attest:

Attesting Officer

JAMES E. ROGAN
Director of the United States Patent and Trademark Office